(12) United States Patent
Jeck

(10) Patent No.: US 8,841,618 B2
(45) Date of Patent: Sep. 23, 2014

(54) DEVICE FOR EXAMINING AN OBJECT, IN PARTICULAR FOR INSPECTING PERSONS FOR SUSPICIOUS ITEMS

(71) Applicant: Smiths Heimann GmbH, Wiesbaden (DE)

(72) Inventor: Michael Jeck, Mainz (DE)

(73) Assignee: Smiths Heimann GmbH, Wiesbaden (DE)

( * ) Notice: Subject to any disclaimer, the term of this patent is extended or adjusted under 35 U.S.C. 154(b) by 0 days.

(21) Appl. No.: 13/671,105

(22) Filed: Nov. 7, 2012

(65) Prior Publication Data

US 2013/0126738 A1    May 23, 2013

Related U.S. Application Data

(63) Continuation of application No. PCT/EP2011/001227, filed on Mar. 12, 2011.

(30) Foreign Application Priority Data

May 7, 2010  (DE) .......................... 10 2010 019 880

(51) Int. Cl.
| | | |
|---|---|---|
| *G01N 21/35* | (2014.01) | |
| *G01J 5/02* | (2006.01) | |
| *G01N 21/63* | (2006.01) | |
| *G01N 21/31* | (2006.01) | |
| *G01S 7/04* | (2006.01) | |
| *G01S 13/88* | (2006.01) | |
| *G01V 8/00* | (2006.01) | |
| *G08B 31/00* | (2006.01) | |
| *G01N 29/26* | (2006.01) | |
| *G01T 1/16* | (2006.01) | |
| *H01Q 3/30* | (2006.01) | |
| *H01Q 21/06* | (2006.01) | |

(52) U.S. Cl.
CPC . *G01J 5/02* (2013.01); *G01N 21/63* (2013.01); *G01N 21/314* (2013.01); *G01N 21/35* (2013.01); *G01S 7/04* (2013.01); *G01S 13/887* (2013.01); *G01V 8/005* (2013.01); *G08B 31/00* (2013.01); *G01N 29/26* (2013.01); *G01T 1/16* (2013.01); *H01Q 3/30* (2013.01); *H01Q 21/061* (2013.01)
USPC ...................................... 250/353; 250/339.06

(58) Field of Classification Search
CPC ...... G01N 21/35; G01N 21/314; G01N 21/63
USPC ............ 250/330, 338.1, 339.06, 339.07, 332, 250/336.1
See application file for complete search history.

(56) References Cited

U.S. PATENT DOCUMENTS 3,713,156 A    1/1973  Pothier
4,163,328 A *  8/1979  Sherburne et al. .............. 434/20
(Continued)

FOREIGN PATENT DOCUMENTS

WO    WO 2005/086620 A2    9/2005
WO    WO 2006/105977 A1    10/2006

*Primary Examiner* — Casey Bryant
(74) *Attorney, Agent, or Firm* — Muncy, Geissler, Olds & Lowe, P.C.

(57) ABSTRACT

For examining objects, in particular for inspecting persons for suspicious items, devices having a scanning system for scanning the object and having an evaluating system are known. An optical marking system is provided, which indicates the position of an item classified as suspicious on the object itself or in a mirror image of the object by means of visible light.

10 Claims, 6 Drawing Sheets

(56) References Cited

U.S. PATENT DOCUMENTS

| | | | |
|---|---|---|---|
| 5,455,590 A | 10/1995 | Collins et al. | |
| 6,317,616 B1 * | 11/2001 | Glossop | 600/407 |
| 7,583,221 B2 | 9/2009 | Detlefsen et al. | |
| 7,889,113 B2 | 2/2011 | Cardiasmenos et al. | |
| 8,242,447 B1 * | 8/2012 | Chawla | 250/336.1 |
| 2004/0080448 A1 | 4/2004 | Lovberg et al. | |
| 2004/0149909 A1 | 8/2004 | Vaidya et al. | |
| 2005/0110672 A1 * | 5/2005 | Cardiasmenos et al. | 342/27 |
| 2005/0230604 A1 * | 10/2005 | Rowe et al. | 250/221 |
| 2008/0179526 A1 * | 7/2008 | Xu et al. | 250/339.07 |
| 2009/0008552 A1 * | 1/2009 | Tadano | 250/330 |
| 2011/0168891 A1 * | 7/2011 | van der Weide et al. | 250/334 |

\* cited by examiner

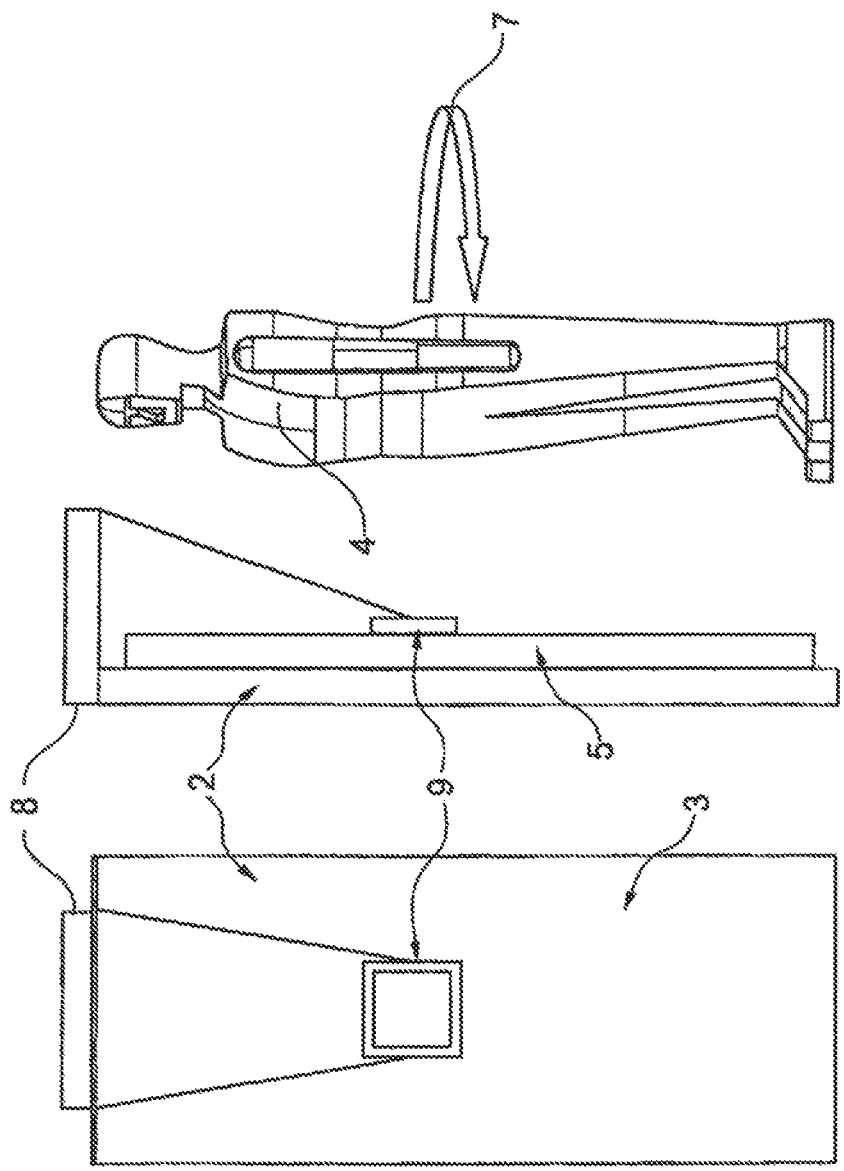

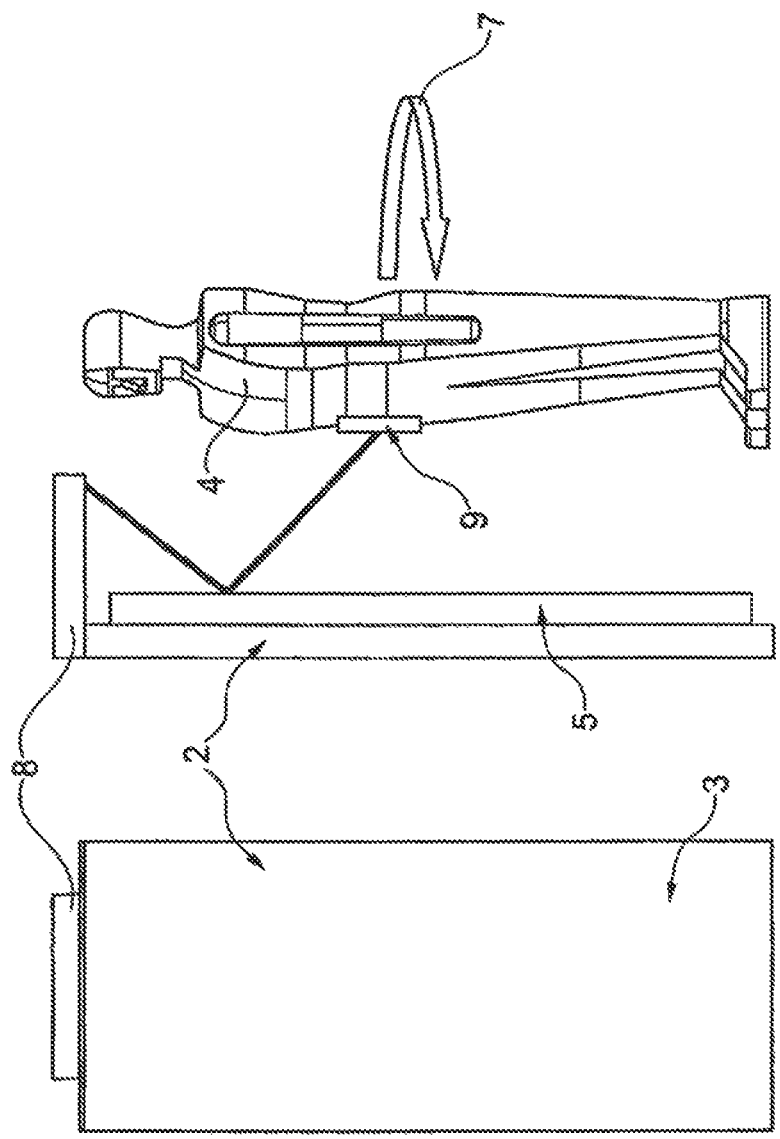

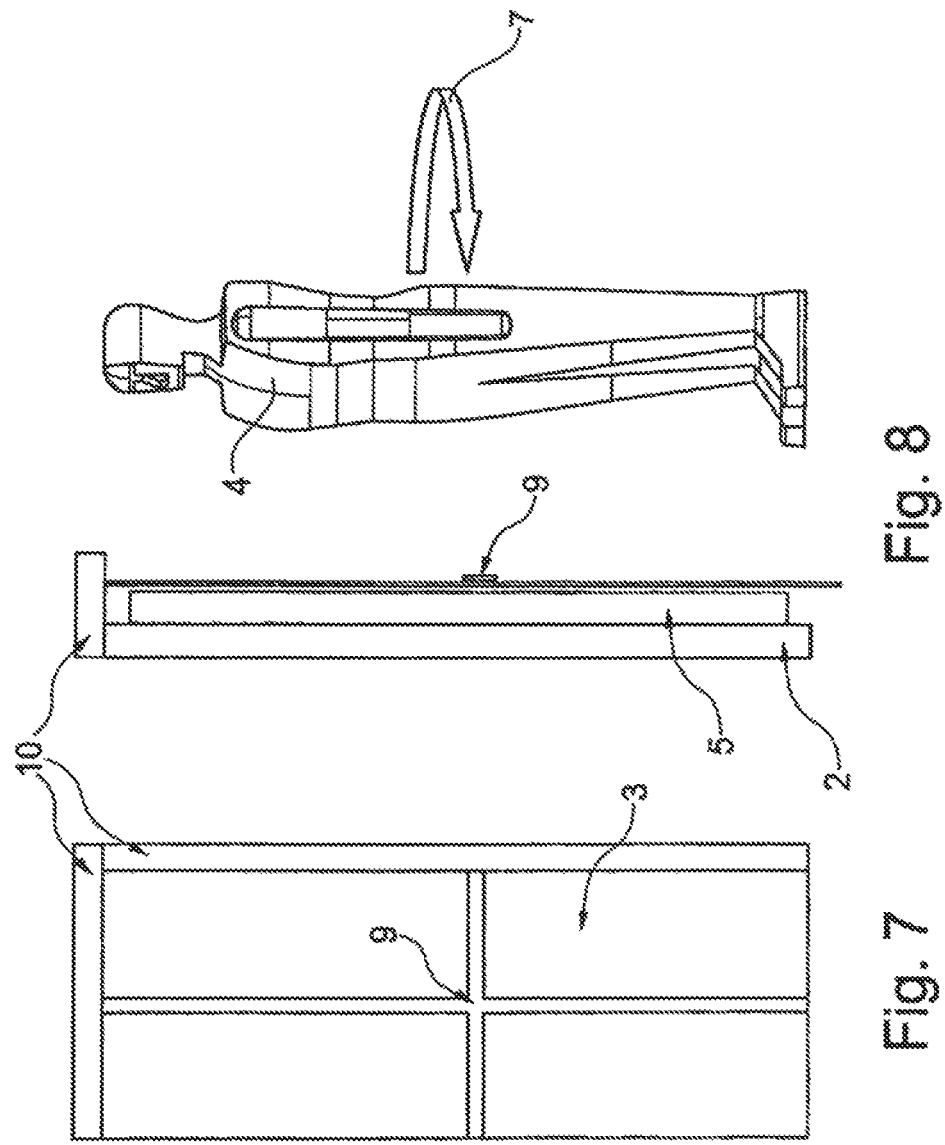

DEVICE FOR EXAMINING AN OBJECT, IN PARTICULAR FOR INSPECTING PERSONS FOR SUSPICIOUS ITEMS

This nonprovisional application is a continuation of International Application No. PCT/EP2011/001227, which was filed on Mar. 12, 2011, and which claims priority to German Patent Application No. DE 10 2010 019 880.3, which was filed in Germany on May 7, 2010, and which are both herein incorporated by reference.

BACKGROUND OF THE INVENTION

1. Field of the Invention

The invention relates to a device for examining objects, in particular for inspecting people for suspicious items, having a scanning system for scanning the object with waves and having an analysis system.

2. Description of the Background Art

In order to inspect people such as airline passengers for suspicious items, contactless inspection systems are known in which the people are scanned with waves in order to detect suspicious items. For example, WO 2006/105977 A1, which corresponds to U.S. Pat. No. 7,583,221, and which is incorporated herein by reference, describes a system in which the person to be examined stands on a platform while being scanned and illuminated successively along his circumference with millimeter waves from a vertical antenna array.

Since artificial elements such as prostheses are visible in an image produced in an examination with millimeter waves, WO 2005/086620 A2, which corresponds to U.S. Pat. No. 7,889,113, proposes taking an additional optical image of the person using an additional camera in order to protect privacy. If suspicious regions are detected in the millimeter wave image, a marking (frame, spot, etc.) is overlaid on the optical image. A disadvantage of this method is the resource expenditure for generating an additional image using an additional camera. Furthermore, problems can arise in superimposing the two images, since they cannot be taken from exactly the same angle. Also, problems with rights of privacy and personality may arise due to the taking of an additional image.

SUMMARY OF THE INVENTION

It is therefore an object of the invention to provide a device for examining objects, in particular for inspecting people for suspicious items, in which the privacy of the person being inspected is protected without the need to expend the additional resources for additional images.

This object is achieved in accordance with the invention in that an optical marking system is present that displays the position of an item categorized as suspicious by means of visible light on the object itself or in a mirror image of the object.

In this solution, the display of the position on the object itself includes, on the one hand, the variant of a display on the object itself being accomplished by, for example, projection of a marking onto a person being inspected. On the other hand, it is possible to display a marking next to the object at the corresponding position. This can be accomplished, for example, by activating a light-emitting diode from a vertical row of light-emitting diodes at the appropriate height, wherein the person being inspected stands next to the light-emitting diodes at a close enough distance that an inspector can extrapolate the corresponding height position to the person.

The scanning system can contain a plurality of antennas arranged in an array, and the antenna array is covered by a cover. The cover is permeable to the waves used, and at least partially reflects visible light to produce a mirror image of the object being inspected. An optical marking system shows, by means of visible light, the position of an item categorized as suspicious in the mirror image of the object produced on the cover.

The cover that at least partially reflects visible light offers a great number of possibilities for displaying the position of an item categorized as suspicious in the mirror image of the object by means of visible light, and also for reflecting marking rays onto the object itself.

Thus it is possible to project a light marking onto the cover, for example by means of a digital projector.

It is likewise possible to project a marking onto the corresponding location on the object being inspected, with it then being possible to observe the marking on the object itself or on the mirror image of the object.

The marking can be produced on the cover by a row of light sources that are arranged on at least two edges of the array and are individually controllable. The position of the suspicious item can then be indicated as the intersection point between at least two light rays that are produced by light sources that have been switched on.

Another embodiment has arranged in the array between the antennas, a plurality of individually controllable light sources whose light passes through the partially permeable cover and in this way marks the position of a suspicious item. In this embodiment, the image viewed by the inspector is independent of his location. Consequently, no corrections in this regard are needed.

The scanning system can use electromagnetic millimeter waves for scanning an object. In this embodiment, the scanning system can be a phased array radar system having transmitting and receiving antennas and also having reflection antennas that are arranged in an array. Alternatively, a scanning system with millimeter waves can also be used in which transmitting and receiving antennas are arranged in an array, wherein the received millimeter waves are analyzed according to the SAR principle, the pulsed radar principle, or the FMCW radar principle. Then the array of transmitting and receiving antennas includes a cover and a marking system according to the invention.

As a further alternative, the use of a scanning system is also possible in which X-rays are used for scanning an object and, for example, X-rays scattered by the object are analyzed. In like manner, it is possible to use a scanning system that scans the objects with ultrasonic waves.

In the case of millimeter wave scanning, the cover of the antenna array has, for example, an extremely thin, visible-light-reflecting metallic layer that the millimeter waves can pass through, or of a material that partially reflects visible light, such as a Plexiglas plate with a dark background, which is likewise permeable to millimeter waves.

In a further embodiment, the object can be a plurality of people, luggage, suitcases, cargo, containers, etc.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIGS. 2 and 3 show front and side views of the antenna array with the optical marking system, FIGS. 5 and 6 show front and side views of a device in which a marking is projected onto the object being inspected, FIGS. 7 and 8 show front and side views of a device with a marking system in which individually controllable light sources produce light rays.

DETAILED DESCRIPTION

Figure 1:
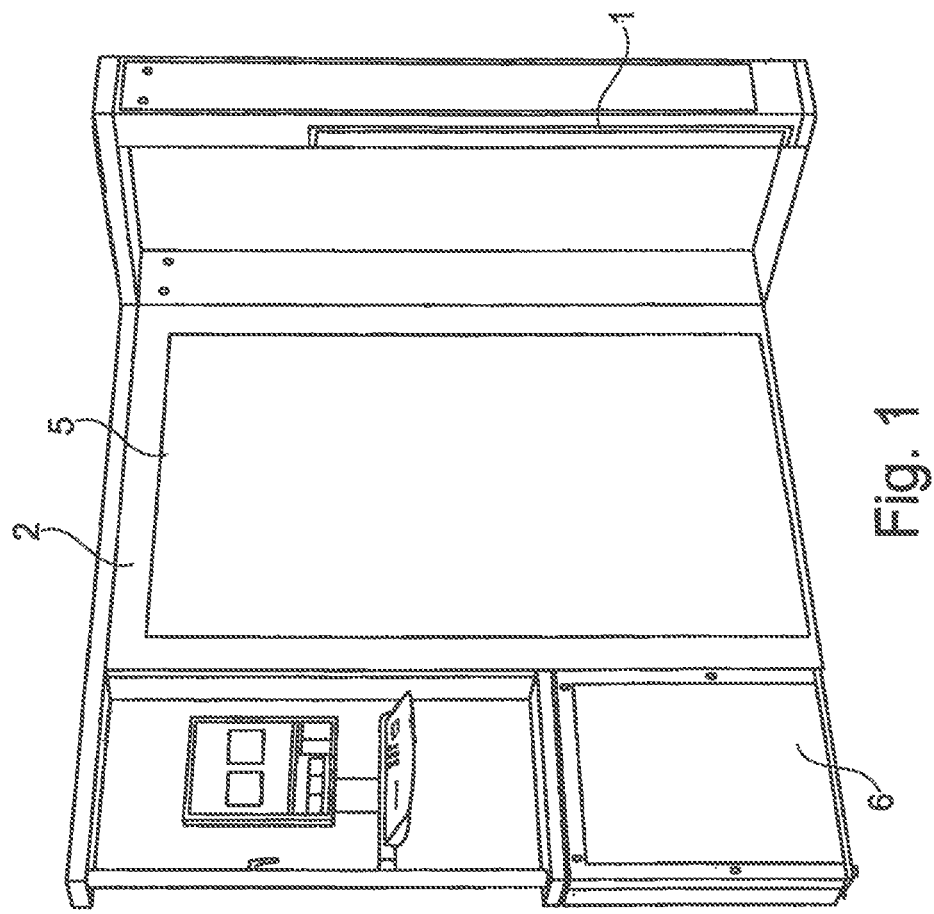
FIG. 1 shows a device according to the invention in a perspective view.

In the exemplary embodiments described below and shown in the figures, a so-called phased array radar system is used as the preferred scanning system. This system has transmitting and receiving antennas 1, which are arranged in a vertical row and transmit and receive millimeter waves. The transmitted millimeter waves are focused in space by a plurality of reflection antennas 3 arranged in an array 2. The test object, a passenger 4 standing upright in the example, is illuminated with these waves. The millimeter waves reflected by the test object (passenger 4) are received by the receiving antennas 1 and analyzed by an analysis system.

In place of a phased array radar system with reflection antennas 3, a scanning system may also be used in which the transmitting and receiving antennas for millimeter waves are arranged in an array and the received millimeter waves are analyzed using a different system.

Alternatively, scanning systems can also be used in which the objects are scanned with other waves, for example with X-ray radiation or with ultrasonic waves.

The antenna array 2 (including reflection antennas 3 in the exemplary embodiment) is arranged to stand vertically. It is covered by a plate-like cover 5, which is permeable to millimeter waves and at the same time at least partially reflects visible light in order to produce a mirror image of the object 4 (in the example of the passenger).

If total reflection of visible light is desired, then the cover 5 preferably has an extremely thin metallic layer that reflects visible light, through which millimeter waves can penetrate. If partial reflection of visible light is desired, then the cover 5 has a plate that is permeable to visible light, in particular a Plexiglas plate, with a dark background, which likewise is permeable to millimeter waves.

In addition, the device includes an analysis system 6, which generates image data from the received millimeter waves; the image data are used to detect suspicious regions. Ascertainment of a suspicious region in the test object can be accomplished either by means of a stored algorithm, which decides whether artificial or natural human substances are present in passengers 4, for example. Or a graphic representation is generated that an operator uses to detect a suspicious region in the millimeter wave image.

Since the device described is used to examine passengers 4 who are standing upright, the antenna array 2 is arranged to stand upright. During the inspection, the passenger 4 rotates 360° as shown by the arrow 7 so that all sides can be examined. Preferably, image data for a video are prepared from the values received during the rotation, and these data are subsequently analyzed with regard to suspicious areas.

Figure 4:
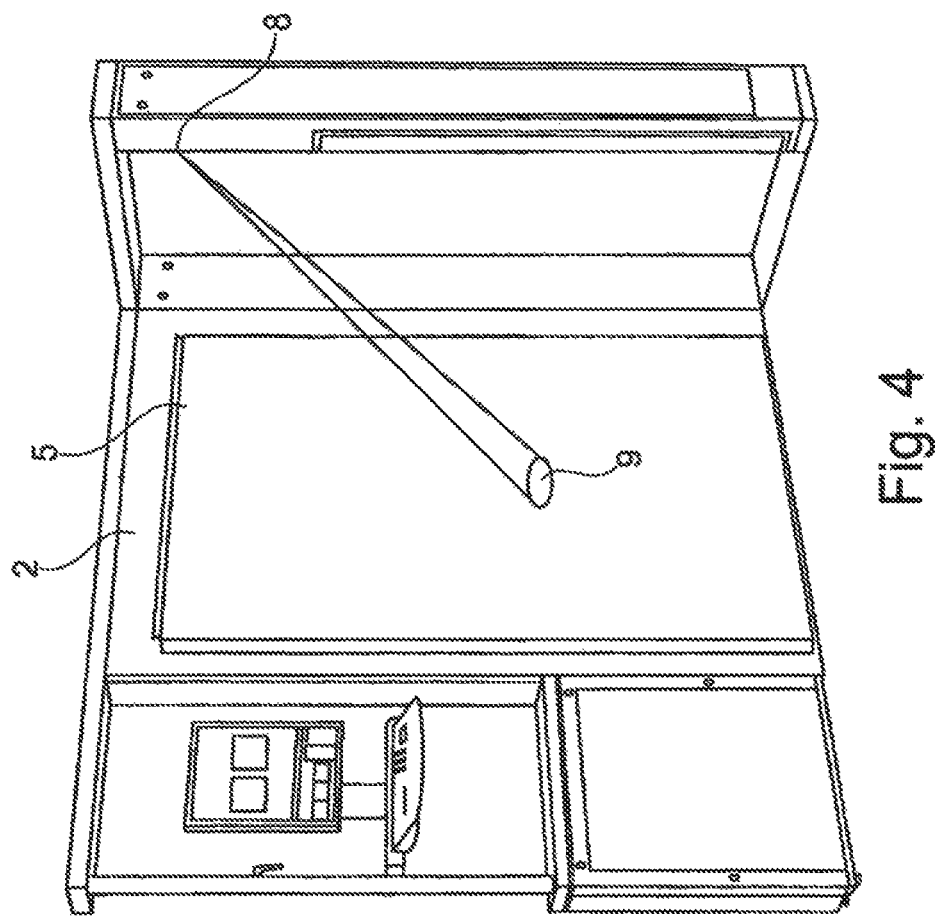
FIG. 4 shows an oblique view of a device with a spot being marked.

FIGS. 2 through 4 show a device that contains a marking system that projects a light marking 9 onto the cover 5 by means of an optical system 8. The optical system 8 contains a digital projector or a similar device that emits a visible light as a frame, spot, etc., for producing a marking on the cover 5. The optical system 8 here is designed such that the marking 8 can be projected to any location on the cover 5.

If the analysis system detects a suspicious region at a certain point on the passenger 4, the marking system projects a marking 9 onto the cover 5 at the corresponding location in the mirror image of the passenger 4. Without violating the privacy of the passenger 4, it is thus possible to indicate to an inspector whether, and where, a suspicious location must be inspected more closely on the passenger 4. Both the passenger 4 and the inspector standing behind him see only the mirror image of the passenger 4 with the superposed marking. Further details from the millimeter wave image are not visible.

In FIG. 2, a projected frame is shown as the marking 9, and in FIG. 4 the projected marking 9 is a spot.

In the embodiment shown in FIGS. 5 and 6, the cover 5 is made of a material that totally reflects visible light. The marking system includes an optical system 8 that projects the marking 9 onto the corresponding location on the test object, which is to say onto the passenger 4 in the example. The passenger 4 and the inspector standing behind him can see the passenger 4 with the projected marking 9 in person or as a mirror image. Preferably the marking 9 is projected onto the object being inspected via a reflection on the cover 5. This exemplary embodiment has the advantage that the mirror image showing the passenger 4 and the marking 4 can be observed without distortion regardless of where the inspector is positioned. Corrections for adapting to the viewer's position are not necessary.

Figure 9:
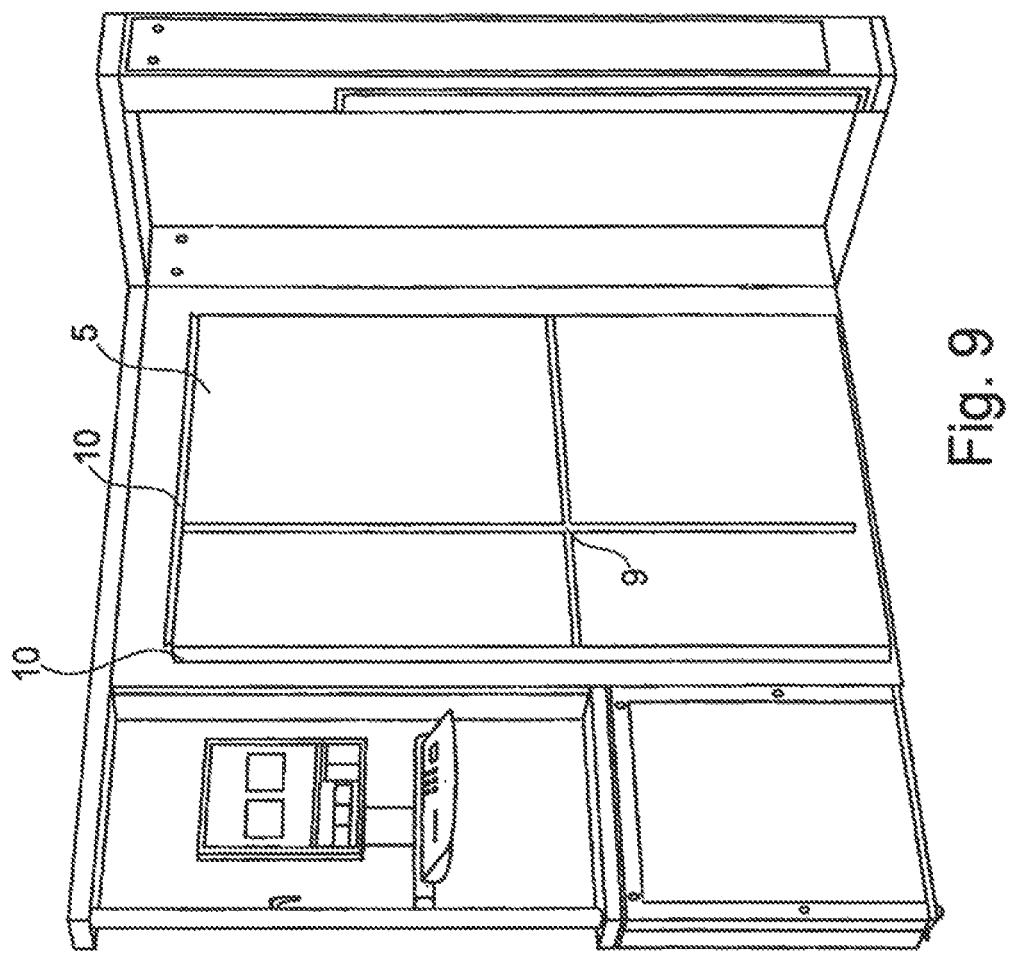
FIG. 9 shows an oblique view of a device from FIGS. 7 and 8.

FIGS. 7-9 show an exemplary embodiment in which the marking 9 on the cover 5 is produced by a row of light sources 10, which are arranged on at least two edges of the array 2 and hence of the cover 5. The light sources 10 can be controlled individually and when they are switched on each generate one light ray that falls across the cover 5 as a stripe. The position of a suspicious item is displayed as an intersection point of at least two light rays that are produced by switching on the light sources 10 at appropriate positions. LEDs are preferably used as light sources.

In another embodiment not shown in the figures, a plurality of individually controllable light sources are arranged between the antennas 3 in the array 2. The light sources are distributed over the entire array 2, with LEDs preferably being used. The cover 5 is partially permeable to visible light, so the light from the light sources shines through the cover 5. In this way, the position of a suspicious item can be marked in the mirror image on the cover 5 by the visible light emitted by the light sources and passing through the cover 5. To this end, the light sources located at the corresponding positions are switched on.

In another embodiment, at least one row of individually controllable light sources is present that preferably are arranged vertically above one another. The row of light sources, preferably LEDs, is arranged such that a passenger can stand next to them. For example, they can be arranged in one of the vertical members of the archway shown on the right-hand side in FIG. 1. The height position of an item categorized as suspicious on the passenger is then indicated to the inspector by the lighting of the light source located at the corresponding height while the passenger stands next to the row of light sources.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A device for examining an object, the device comprising:
    a scanning system for scanning the object with waves;
    an analysis system configured to receive the waves from the scanning system and to generate image data from the waves; and
    an optical marking system configured to indicate a position of an item on the object detected by the analysis system via visible light,
    wherein the scanning system contains a plurality of antennas arranged in an array,
    wherein the antenna array is covered by a cover that is permeable to the waves used and at least partially reflects visible light to produce a mirror image of the object, and
    wherein the optical marking system indicates the position of the item in the mirror image of the object produced on the cover.

2. The device according to claim 1, wherein an optical system projects a light marking onto the cover.

3. The device according to claim 2, wherein a row of individually controllable light sources is arranged on an edge of the array, the light sources being configured to be activated individually to mark a position of a suspicious item via light rays.

4. The device according to claim 1, wherein a plurality of individually controllable light sources are arranged between the antennas in the array whose light passes through the partially permeable cover, marking the position of a suspicious item as a mirror image.

5. The device according to claim 1, wherein the scanning system uses electromagnetic millimeter waves for scanning an object.

6. The device according to claim 5, wherein the scanning system is a phased array radar system with reflection antennas that are arranged in an array.

7. The device according to claim 1, wherein the scanning system uses electromagnetic millimeter waves for scanning an object, and
    wherein the cover is made of a visible-light-reflecting metallic layer that the millimeter waves can pass through.

8. The device according to claim 1, wherein the scanning system uses electromagnetic millimeter waves for scanning an object, and
    wherein the cover is made of a material that is permeable to visible light, that is provided with a dark background for partial reflection.

9. A device for examining an object, the device comprising:
    a scanning system for scanning the object with waves;
    a cover covering the scanning system;
    an analysis system configured to receive the waves from the scanning system and to generate image data from the waves; and
    an optical marking system configured to indicate a position of an item on the object detected by the analysis system via visible light on the object itself or in a mirror image of the object,
    wherein the optical marking system indicates the position of the item on the cover.

10. A device for examining an object, the device comprising:
    a scanning system for scanning the object with waves;
    an analysis system configured to receive the waves from the scanning system and to generate image data from the waves; and
    an optical marking system configured to indicate a position of an item on the object detected by the analysis system via visible light on the object itself or in a mirror image of the object,
    wherein the optical marking system is configured to project light onto the object itself or in the mirror image of the object.

* * * * *